US008956400B2

(12) United States Patent
Beach et al.

(10) Patent No.: US 8,956,400 B2
(45) Date of Patent: Feb. 17, 2015

(54) HELICAL STENT

(75) Inventors: Bradley Beach, Belmar, NJ (US); Janet Burpee, Fairhaven, NJ (US)

(73) Assignee: Flexible Stenting Solutions, Inc.

( * ) Notice: Subject to any disclaimer, the term of this patent is extended or adjusted under 35 U.S.C. 154(b) by 390 days.

(21) Appl. No.: 11/497,069

(22) Filed: Aug. 1, 2006

(65) Prior Publication Data

US 2007/0129786 A1 Jun. 7, 2007

Related U.S. Application Data

(60) Provisional application No. 60/731,724, filed on Oct. 31, 2005.

(51) Int. Cl.
*A61F 2/06* (2013.01)
*A61F 2/915* (2013.01)
*A61F 2/91* (2013.01)
A61F 2/88 (2006.01)
A61F 2/82 (2013.01)
A61F 2/848 (2013.01)

(52) U.S. Cl.
CPC . *A61F 2/915* (2013.01); *A61F 2/91* (2013.01); A61F 2/88 (2013.01); A61F 2002/823 (2013.01); A61F 2002/8486 (2013.01); A61F 2002/91533 (2013.01); A61F 2002/91558 (2013.01); A61F 2250/0039 (2013.01)
USPC .................................................. 623/1.15

(58) Field of Classification Search
USPC ............. 623/1.22, 1.11, 1.31, 1.3, 1.15, 1.16, 623/1.36, 1.37, 1.35, 1.13–1.2; 606/192, 606/194, 108
See application file for complete search history.

(56) References Cited

U.S. PATENT DOCUMENTS

| 5,275,622 | A | * | 1/1994 | Lazarus et al. | 623/1.11 |
| 5,292,321 | A | * | 3/1994 | Lee | 606/28 |
| 5,449,373 | A | * | 9/1995 | Pinchasik et al. | 606/198 |
| 5,575,818 | A | * | 11/1996 | Pinchuk | 623/1.15 |
| 5,591,197 | A | * | 1/1997 | Orth et al. | 623/1.16 |
| 5,591,198 | A | * | 1/1997 | Boyle et al. | 623/1.22 |
| 5,649,949 | A | * | 7/1997 | Wallace et al. | 606/191 |
| 5,749,919 | A | * | 5/1998 | Blanc | 623/1.22 |
| 5,755,781 | A | * | 5/1998 | Jayaraman | 623/1.16 |
| 5,776,142 | A | * | 7/1998 | Gunderson | 623/1.11 |
| 5,810,872 | A | | 9/1998 | Kanesaka et al. | 606/198 |
| 5,891,192 | A | | 4/1999 | Murayama et al. | 623/1 |
| 5,897,588 | A | * | 4/1999 | Hull et al. | 623/1.15 |

(Continued)

FOREIGN PATENT DOCUMENTS

| EP | 1 452 151 | 9/2004 | A61F 2/06 |
| WO | 01/26584 | 4/2001 | A61F 2/06 |

*Primary Examiner* — Jocelin Tanner

(57) ABSTRACT

The present invention relates to a stent providing a high percentage of vessel coverage, preferably at least about 50% of the portion of the vessel covered by the helical elements of the stent. The stent comprises helical elements interposed between strut members in which the helical elements are connected to the strut members by linking elements. The portion of the stent having helical elements provides a high percentage of covered area for example, in an aneurysm area. The linking elements provide part of a mechanism that allows vessel coverage to be maintained as the stent is deployed from a crimped state to an expanded state allowing the helical elements to change its helix angle (the angle at which the helical elements progresses around the circumference and along the length of the stent) and thereby the pitch of the helical elements as the stent is expanded.

29 Claims, 12 Drawing Sheets

(56) References Cited

U.S. PATENT DOCUMENTS

| | | | |
|---|---|---|---|
| 5,925,061 A | 7/1999 | Ogi et al. | 606/198 |
| 5,954,743 A * | 9/1999 | Jang | 623/1.15 |
| 5,961,548 A * | 10/1999 | Shmulewitz | 623/1.35 |
| 6,042,597 A * | 3/2000 | Kveen et al. | 623/1.15 |
| 6,117,165 A | 9/2000 | Becker | 623/1 |
| 6,156,062 A | 12/2000 | McGuinness | 623/1.11 |
| 6,165,210 A | 12/2000 | Lau et al. | 623/1.12 |
| 6,241,757 B1 * | 6/2001 | An et al. | 623/1.1 |
| 6,264,690 B1 * | 7/2001 | Von Oepen | 623/1.3 |
| 6,287,333 B1 | 9/2001 | Appling et al. | 623/1.22 |
| 6,416,543 B1 | 7/2002 | Hilaire et al. | 623/1.16 |
| 6,432,132 B1 | 8/2002 | Cottone et al. | 623/1.15 |
| 6,503,270 B1 | 1/2003 | Richter et al. | 623/1.15 |
| 6,506,211 B1 | 1/2003 | Skubitz et al. | 623/1.15 |
| 6,579,308 B1 * | 6/2003 | Jansen et al. | 623/1.15 |
| 6,585,758 B1 * | 7/2003 | Chouinard et al. | 623/1.16 |
| 6,599,314 B2 * | 7/2003 | Mathis | 623/1.11 |
| 6,602,281 B1 * | 8/2003 | Klein | 623/1.15 |
| 6,613,077 B2 | 9/2003 | Gilligan et al. | 623/1.12 |
| 6,663,664 B1 | 12/2003 | Pacetti | 623/1.2 |
| 6,706,062 B2 | 3/2004 | Vardi et al. | 623/1.15 |
| 6,709,452 B1 * | 3/2004 | Valimaa et al. | 623/1.15 |
| 6,730,117 B1 | 5/2004 | Tseng et al. | 623/1.16 |
| 6,746,475 B1 | 6/2004 | Rivelli, Jr. | 623/1.15 |
| 6,761,731 B2 * | 7/2004 | Majercak | 623/1.11 |
| 6,821,292 B2 | 11/2004 | Pazienza et al. | 623/1.15 |
| 6,860,899 B1 * | 3/2005 | Rivelli, Jr. | 623/1.22 |
| 6,878,162 B2 | 4/2005 | Bales et al. | 623/1.15 |
| 6,896,696 B2 | 5/2005 | Doran et al. | 623/1.15 |
| 6,899,730 B1 * | 5/2005 | Rivelli, Jr. | 623/1.15 |
| 6,945,993 B2 | 9/2005 | Kveen et al. | 623/1.15 |
| 6,949,120 B2 | 9/2005 | Kveen et al. | 623/1.15 |
| 6,969,401 B1 | 11/2005 | Marotta et al. | 623/1.15 |
| 6,969,402 B2 * | 11/2005 | Bales et al. | 623/1.15 |
| 7,637,939 B2 * | 12/2009 | Tischler | 623/1.22 |
| 2002/0002400 A1 | 1/2002 | Drasker et al. | 623/1.15 |
| 2002/0022877 A1 * | 2/2002 | Mueller et al. | 623/1.16 |
| 2002/0042646 A1 | 4/2002 | Wall | 623/1.13 |
| 2002/0143390 A1 | 10/2002 | Ishii | 623/1.15 |
| 2002/0165603 A1 | 11/2002 | Thornton et al. | 623/1.13 |
| 2002/0193868 A1 | 12/2002 | Mitelberg et al. | 623/1.15 |
| 2003/0045925 A1 * | 3/2003 | Jayaraman | 623/1.16 |
| 2003/0050690 A1 | 3/2003 | Kveen et al. | 623/1.15 |
| 2003/0097172 A1 * | 5/2003 | Shalev et al. | 623/1.31 |
| 2003/0144729 A1 * | 7/2003 | Bicek et al. | 623/1.16 |
| 2003/0149473 A1 | 8/2003 | Chouinard et al. | 623/1.15 |
| 2003/0149474 A1 | 8/2003 | Becker | 623/1.15 |
| 2003/0204244 A1 | 10/2003 | Stiger | 623/1.16 |
| 2004/0002753 A1 | 1/2004 | Burgermeister et al. | 623/1.15 |
| 2004/0088044 A1 * | 5/2004 | Brown et al. | 623/1.15 |
| 2004/0122504 A1 | 6/2004 | Hogendijk | 623/1.15 |
| 2004/0149294 A1 | 8/2004 | Gianchandani et al. | 128/879 |
| 2004/0158306 A1 | 8/2004 | Mitelberg et al. | 623/1.2 |
| 2004/0172123 A1 | 9/2004 | Lootz et al. | 623/1.15 |
| 2004/0186556 A1 * | 9/2004 | Hogendijk et al. | 623/1.16 |
| 2004/0215325 A1 | 10/2004 | Penn et al. | 623/1.15 |
| 2004/0220663 A1 | 11/2004 | Rivelli, Jr. | 623/1.22 |
| 2004/0236401 A1 | 11/2004 | Shin et al. | 623/1.13 |
| 2004/0260384 A1 | 12/2004 | Allen | 623/1.12 |
| 2005/0015136 A1 | 1/2005 | Ikeuchi et al. | 623/1.15 |
| 2005/0033410 A1 | 2/2005 | Hogendijk et al. | 623/1.15 |
| 2005/0080479 A1 | 4/2005 | Feng et al. | 623/1.15 |
| 2005/0085899 A1 | 4/2005 | Thornton | 623/1.16 |
| 2005/0090888 A1 | 4/2005 | Hines et al. | 623/1.11 |
| 2005/0096725 A1 | 5/2005 | Pomeranz et al. | 623/1.15 |
| 2005/0096727 A1 | 5/2005 | Allen et al. | 623/1.15 |
| 2005/0096732 A1 | 5/2005 | Marotta et al. | 623/1.15 |
| 2005/0113903 A1 | 5/2005 | Rosenthal et al. | 623/1.15 |
| 2005/0149164 A1 | 7/2005 | Rivelli, Jr. | 623/1.11 |
| 2005/0192661 A1 | 9/2005 | Griffen et al. | 623/1.15 |
| 2006/0025849 A1 | 2/2006 | Kaplan et al. | 623/1.15 |

\* cited by examiner

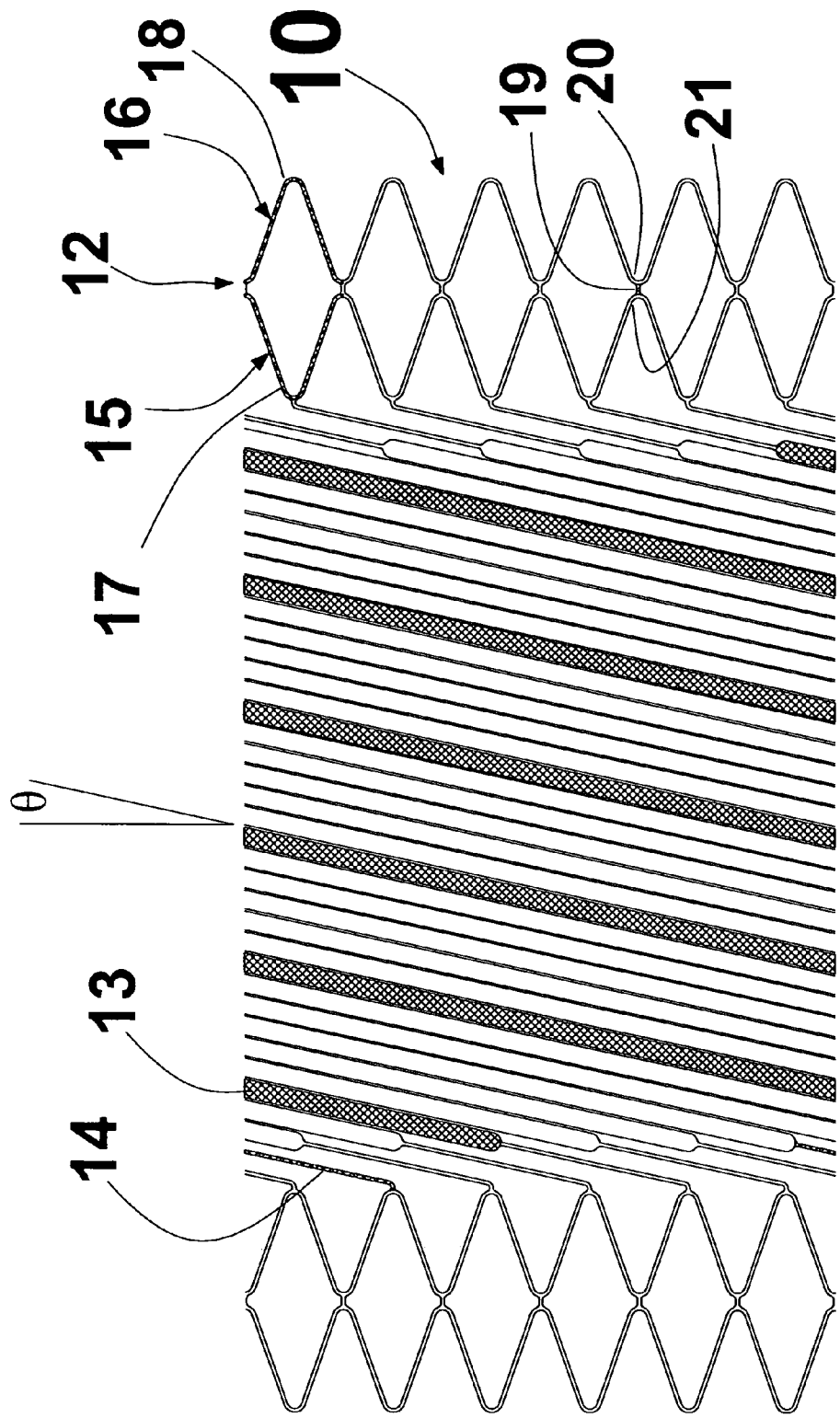

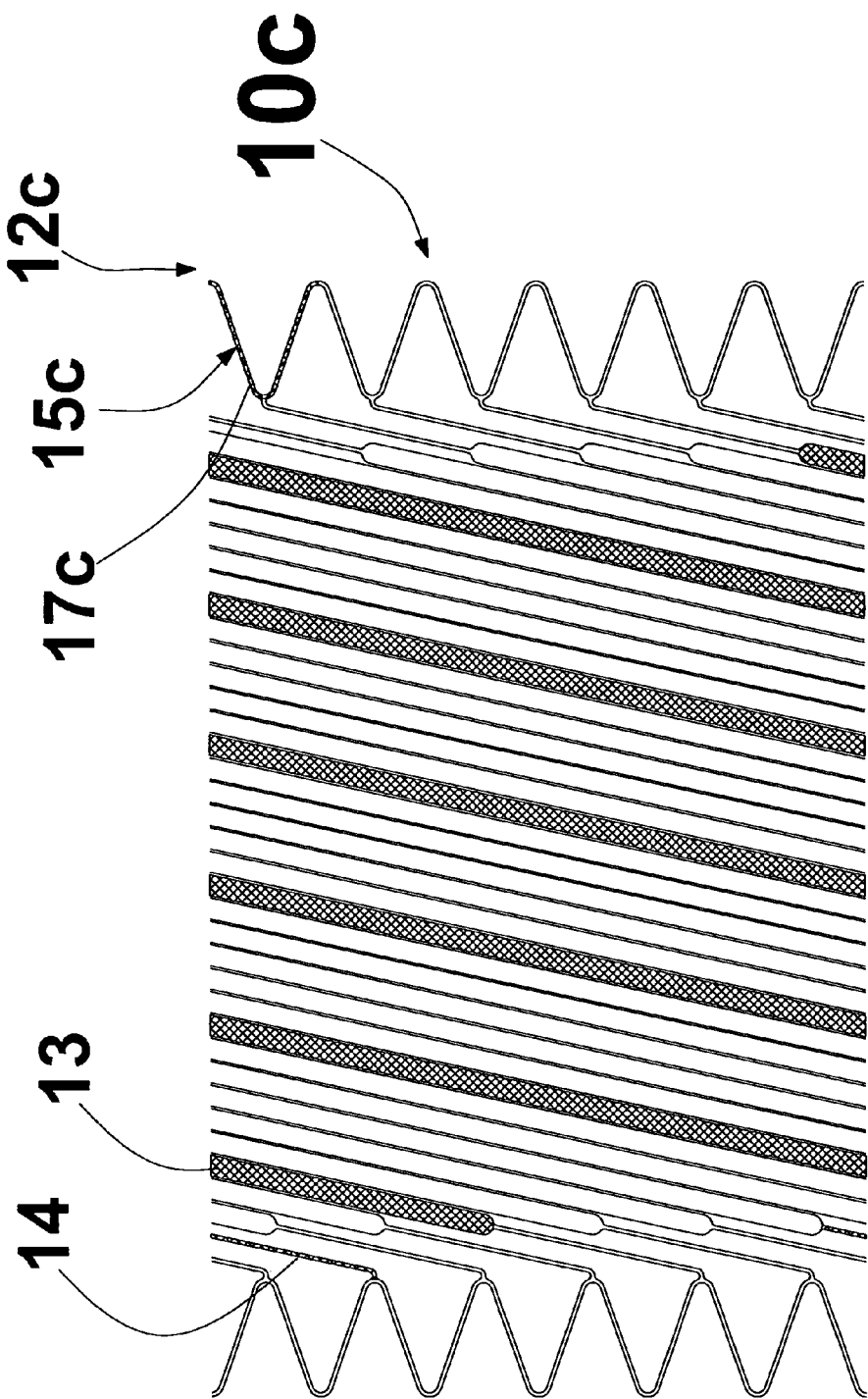

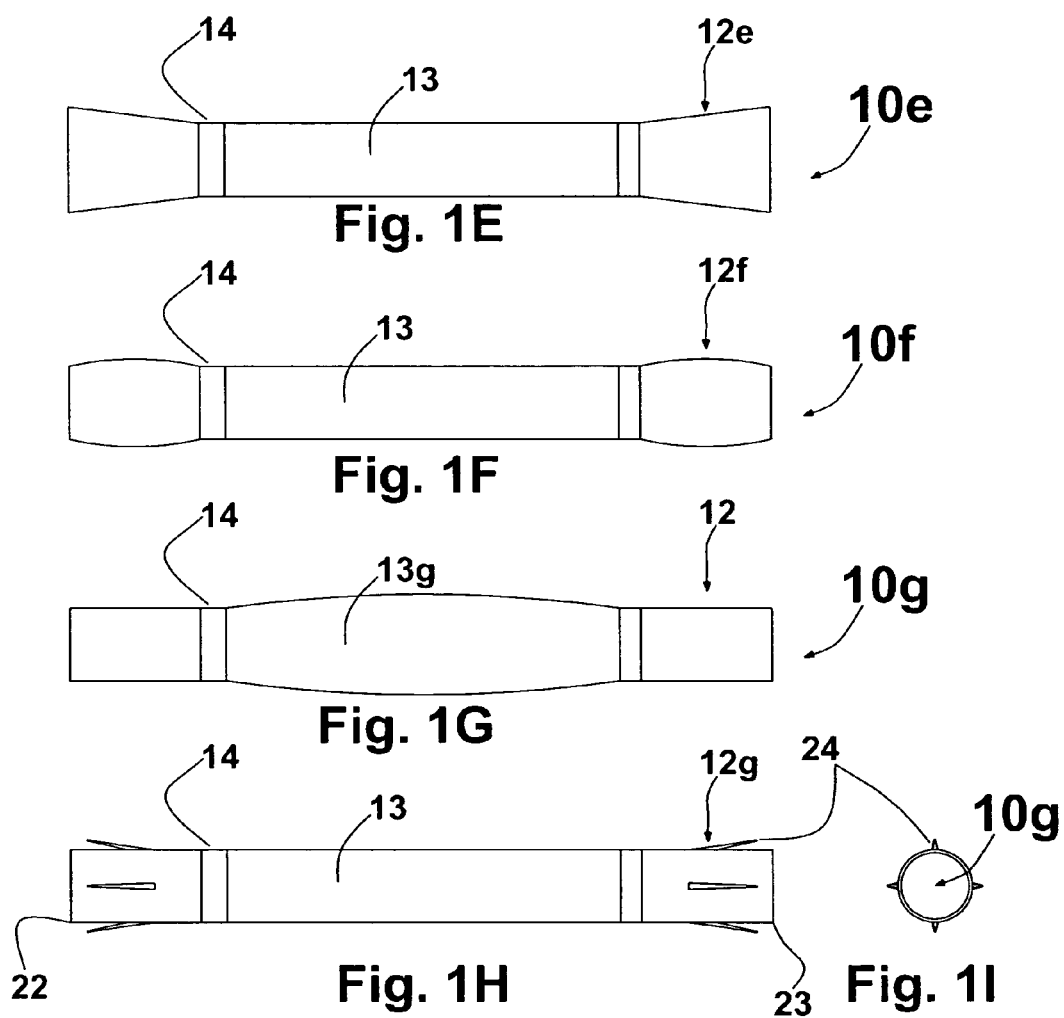

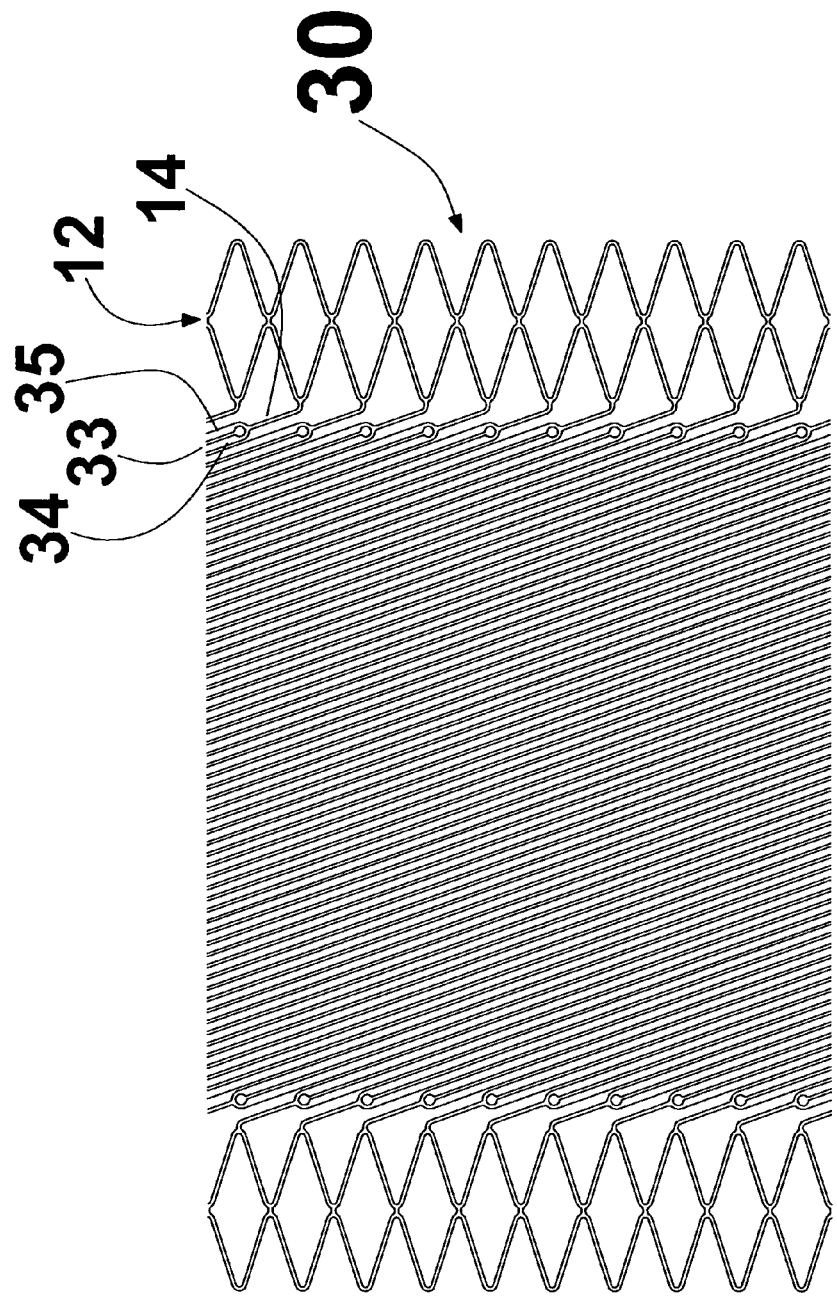

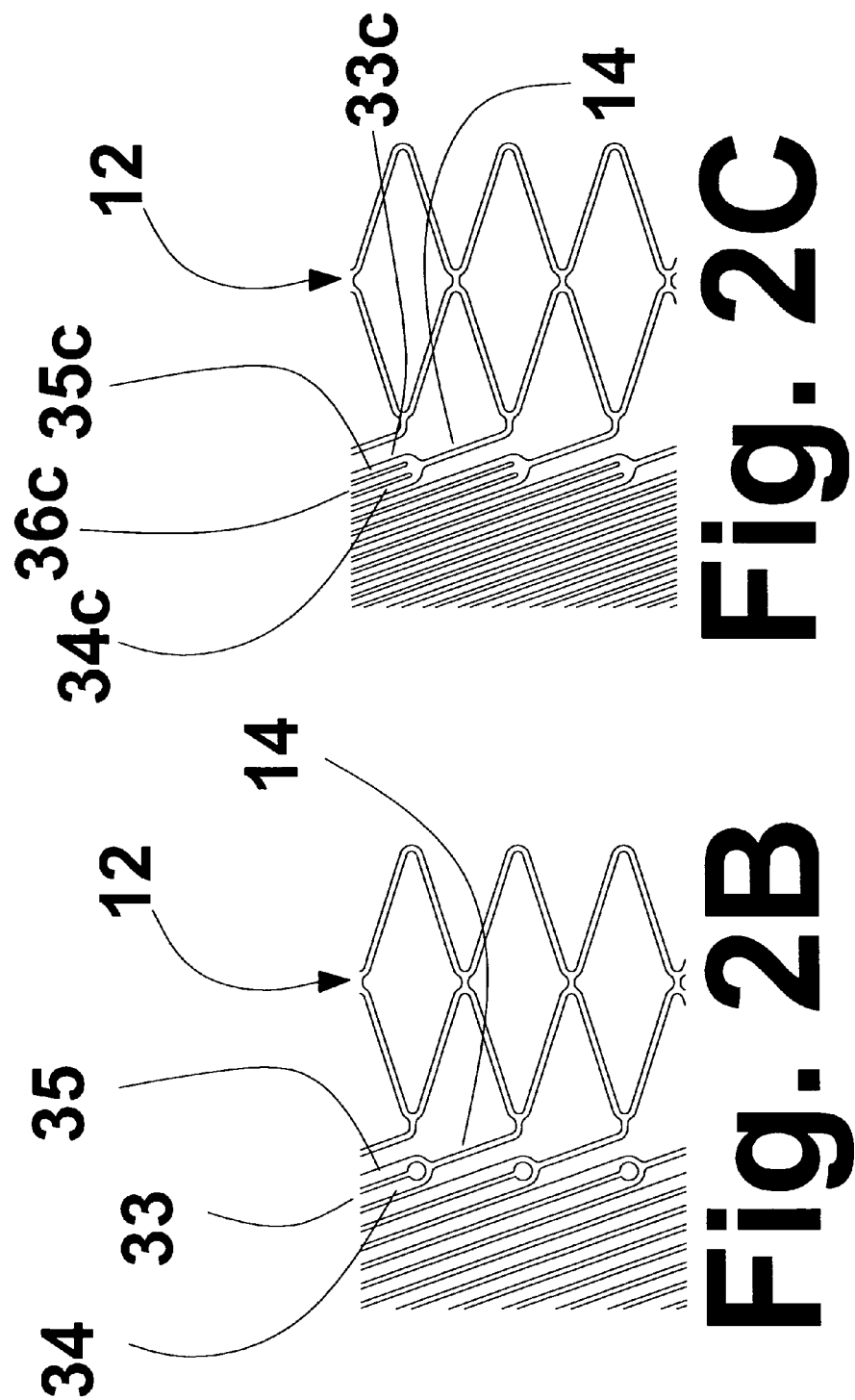

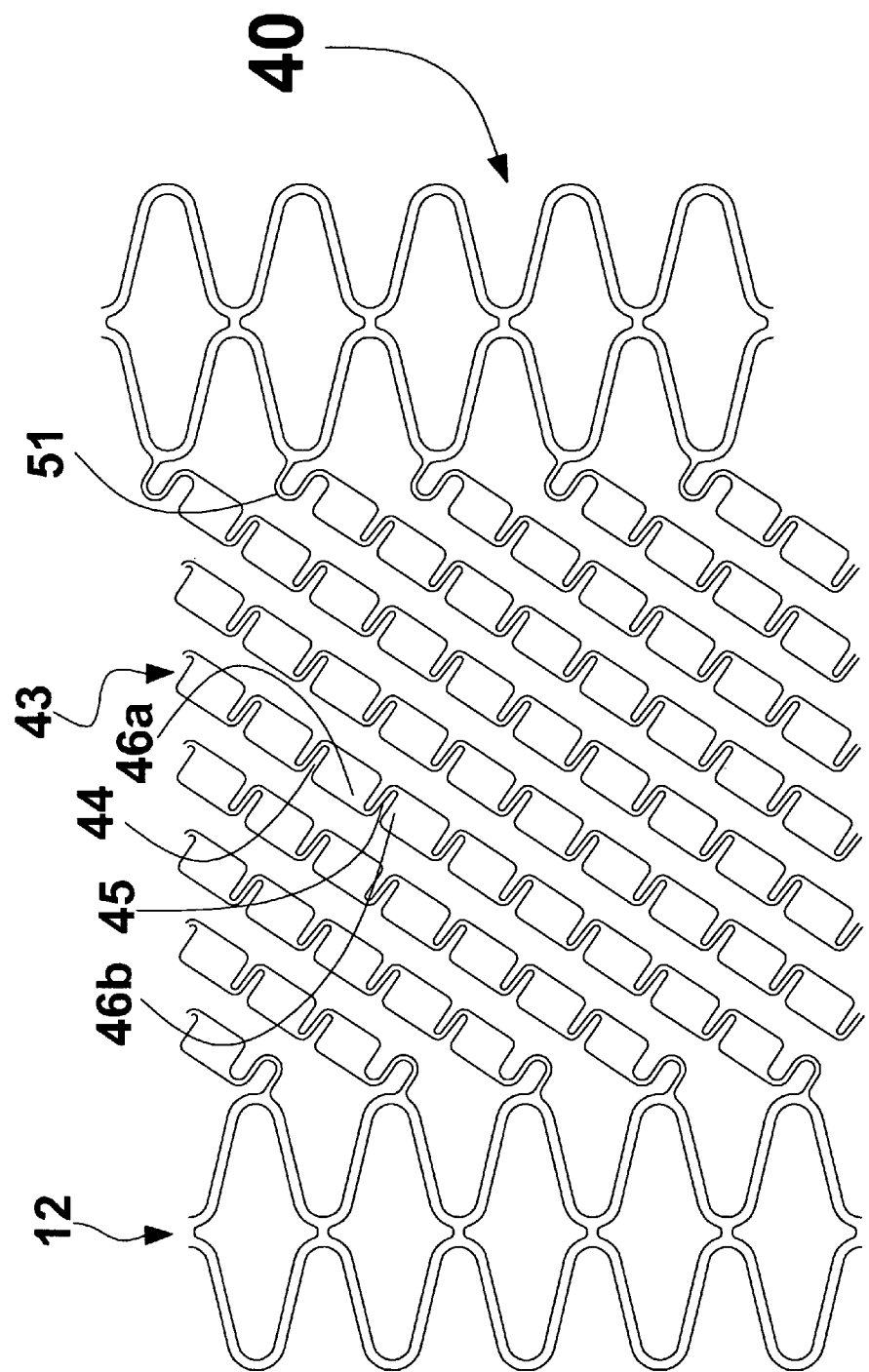

HELICAL STENT

CROSS REFERENCE TO RELATED APPLICATION

This application claims the benefit of U.S. Provisional Patent Application No. 60/731,724 filed Oct. 31, 2005, the entirety of which is hereby incorporated by reference into this application. This application is related to U.S. patent application Ser. No. 11/250,226, filed Oct. 14, 2005, the entirety of which is incorporated by reference into this application.

BACKGROUND OF THE INVENTION

1. Field of the Invention

The invention relates to a stent-like structure which in one embodiment can be used for treating neurovascular or brain aneurysms.

2. Description of Related Art

A stent is a tubular structure that in a radially compressed state (crimped state) may be inserted into a vessel in the body. Once located in the vessel, the stent may be expanded radially to a predefined size (expanded state). Stents are typically characterized as balloon expanding or self expanding. A balloon expanding stent requires a balloon, which is part of the delivery system, to expand the stent from the crimped state to an expanded state. A self expanding stent is designed, through choice of material, geometry, or manufacturing techniques, to expand from a crimped state to an expanded state once the stent is released into the intended vessel.

A stent is commonly thought of as a device that opens a narrowed artery. A stent-like structure has similar characteristics to a stent, but may not open or support an artery. Unless otherwise indicated, as used hereafter, the term "stent" will be understood to encompass both a stent and stent-like structure.

An aneurysm is a weakened area in a vessel that has expanded or bulged. Untreated aneurysms are susceptible to rupture. Stenting of an aneurysm could strengthen the weakened vessel by cutting off significant blood flow to the aneurysm. The reduced blood flow could result in thrombosis in the aneurysm and promote healing regardless of the aneurysm form or shape. Stents have been used to treat aneurysms. Conventional stent grafts have been used to treat Thoracic and Abdominal Aortic Aneurysms. Stent grafts have a metallic stent structure covered by graft material. Stents have also been used experimentally to repair neurovascular aneurysms which were first treated with platinum coils that have migrated over time into the parent vessel. See Pride, Jr. et al., Endovascular problem solving with intravascular stents, *AJNR Am J Neuroradiol.* 2000; 21:532-540.

One system, Boston Scientific's Neuroform Microdelivery Stent System, is described for use with embolic coils. Conventional treatment includes aneurysm clipping, which requires a craniotomy, or aneurysm coiling, placing small platinum or polymer coils in the aneurysm to facilitate thrombosis. The above-described conventional methods for treatment of neurovascular aneurysms have certain drawbacks. Coiling is effective when the aneurysm has a well defined neck (transition from the bulging portion of the vessel to the nominal vessel diameter). If this neck transition is wide or long, coiling is not as effective as the coils tend to migrate and cause other complications, as described in Lownie et al., Endovascular therapy of a large vertebral artery aneurysm using stent and coils, *Can J Neurol Sci* 2000; 27:162-165 and Wanke et al., Treatment of wide-necked intracranial aneurysms with a self-expanding stent system: initial clinical experience, *AJNR Am J Neuroradiol.* 2003; 24:1192-1199. Clipping is very invasive, risky and expensive.

Current coronary stents typically have an expandable "Z" strut scaffolding structure that allows efficient radial expansion and effective vessel dilation. This type of structure requiring a large open area is not expected to be effective for treating neurovascular aneurysms because the large open areas would not inhibit blood flow. In coronary stents, radial expansion is achieved by opening the scaffolding structure to produce a structure that is mostly open area. Coronary stents typically have 75% to 90% open area (10 to 25% vessel coverage).

It is believed that in order for stenting to be effective for treating brain aneurysms, the percent of the vessel covered would need to be at least about 35%. It is desirable to provide a stent for treating neurovascular or brain aneurysms having the percent of the vessel covered of at least about 35%.

SUMMARY OF THE INVENTION

The present invention relates to a stent providing a high percentage of vessel coverage, preferably at least about 50% of the portion of the vessel covered by the helical elements of the stent. The stent comprises helical elements interposed between strut members in which the helical elements are connected to the strut members by linking elements. The strut members provide radial structure of the stent and an anchoring mechanism. The portion of the stent having helical elements provides a high percentage of covered area for example, in an aneurysm area. The linking elements provide part of a mechanism that allows vessel coverage to be maintained as the stent is deployed from a crimped state to an expanded state. In the stent of the present invention, vessel coverage in the expanded state is primarily achieved by shortening the pitch (distance per turn) of the helical elements during radial expansion. The linking element between the strut members and helical elements is part of a mechanism allowing the helical elements to change its helix angle (the angle at which the helical elements progresses around the circumference and along the length of the stent) and thereby the pitch of the helical elements as the stent is expanded.

The invention will be more fully described by reference to the following drawings.

BRIEF DESCRIPTION OF THE DRAWINGS

FIG. 1A is a plan view of a first embodiment of the stent of the present invention including helical elements interposed between strut members and connected to the strut members by flexible linking elements.

FIG. 1C is a plan view of an alternate embodiment of the strut members and flexible linking elements including a single strut ring portion.

FIG. 1E is a schematic profile diagram of an alternative embodiment of the stent of the present invention in which strut members have a flared configuration.

FIG. 1F is a schematic profile diagram of an alternative embodiment of the stent of the present invention in which strut members have a larger diameter than the helical member.

FIG. 1G is a schematic profile diagram of an alternative embodiment of the stent of the present invention in which a helical member has a larger diameter than the stent members.

FIG. 1H is a schematic profile diagram of an alternative embodiment of the stent of the present invention in which strut members include barbs at either end thereof.

FIG. 1I is a schematic profile diagram of an end view of the stent shown in FIG. 1H.

FIG. 2A is a plan view of an alternate embodiment of the present invention having split helical elements interposed between strut members and connected to the strut members by flexible linking elements.

FIG. 2B is a detailed view of FIG. 2A showing a portion of the split helical elements.

FIG. 2C is a detailed view of an alternative embodiment of the helical element comprising a plurality of segments.

FIG. 4 is a plan view of an alternate embodiment of the present invention comprising helical elements with thin diagonal sections with portions of the thin diagonal sections having a reduced width and curved flexible linking elements connecting the helical elements to the strut members.

DETAILED DESCRIPTION OF THE PREFERRED EMBODIMENTS

Figure 1B:
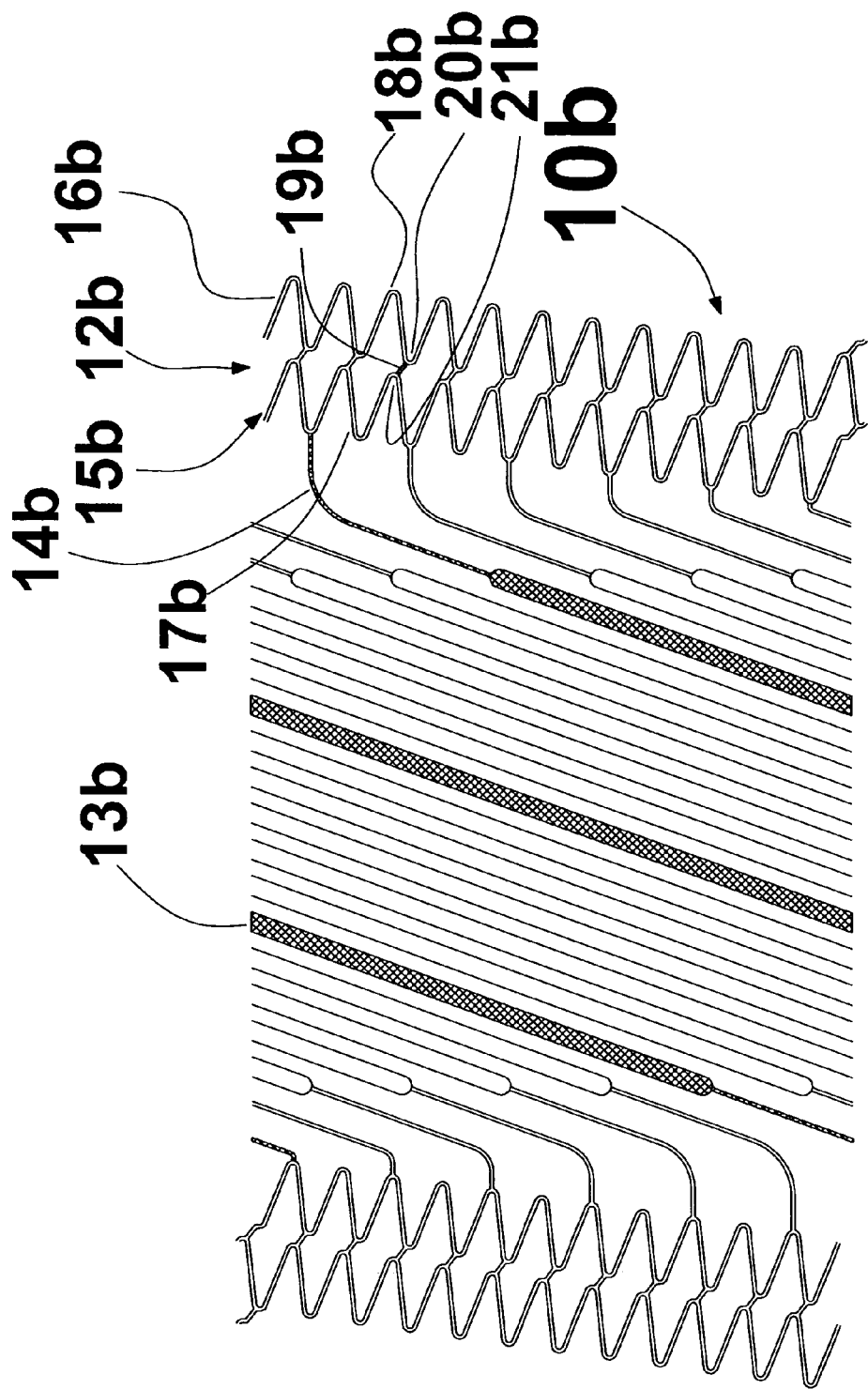
FIG. 1B is a plan view of an alternate embodiment of the strut members and flexible linking elements including helical strut ring portions.

Reference will now be made in greater detail to a preferred embodiment of the invention, an example of which is illustrated in the accompanying drawings. Wherever possible, the same reference numerals will be used throughout the drawings and the description to refer to the same or like parts.

FIG. 1A is a plan view of a first embodiment of stent 10. As used herein, the term plan view will be understood to be a 2 dimensional (2-D) view where the stent has been cut along the axis and laid out flat, such that the bottom edge could be wrapped around a cylinder and connected to the top edge. Unless otherwise indicated all plan views are plan views of the stent in an expanded state. Stent 10 comprises strut members 12, helical elements 13 and flexible linking elements 14. In this representation one of helical elements 13 has been shaded. Strut members 12 comprise one or more strut ring portions 15 and 16. Strut ring portions 15 and 16 comprise respectively a plurality of strut elements 17 and 18. In this representation, one of strut elements 17 and 18 has been shaded. The plurality of strut elements 17 can be integral to one another. The plurality of strut elements 18 can be integral to one another. Connecting elements 19 connect strut elements 17 and 18 together at peaks 20 and 21. Connecting elements 19 can be rigid, flexible or of various predetermined lengths, for example, a helix configuration. Helical elements 13 are arranged in a side-by-side configuration in which each of helical elements 13 is helically wound about an axis of stent 10. Helical elements 13 are expandable radially upon deployment. In this embodiment, each helical element 13 makes more than one rotation about the surface of stent 10. However, they can make a partial rotation or one complete rotation. Strut member 12 generally provides an anchoring mechanism for stent 10 and comprises one or more strut ring portions 15 and 16 depending on the requirements of the stent. Strut ring portions 15 and 16 of strut member 12 provide radial structure and a mechanism for radial expansion of stent 10. In a preferred embodiment, strut member 12 is positioned at either end of stent 10. Strut member 12 being radially expandable upon deployment. Strut ring portions 15 and 16 can be formed of a variety of shapes and sizes to provide desired strength and stiffness upon expansion. For example, strut ring portions 15 and 16 can have a circumferential configuration in which strut ring portions 15 and 16 wrap around a circumference of stent 10 and each connects to itself.

In an alternate embodiment, stent 10b includes strut ring portions 15b and 16b having a helical configuration in which strut ring portions 15b and 16b wrap in a spiral around the circumference of stent 10b and along the length of stent 10b, as shown in FIG. 1B. Flexible linking element 14b can include a curved section for connecting helical element 13b to strut member 12b. Connecting elements 19b connect strut elements 17b and 18b together diagonally at peaks 20b and 21b. Accordingly, adjacent peaks 20b and 21b are offset diagonally from one another.

Figure 1D:
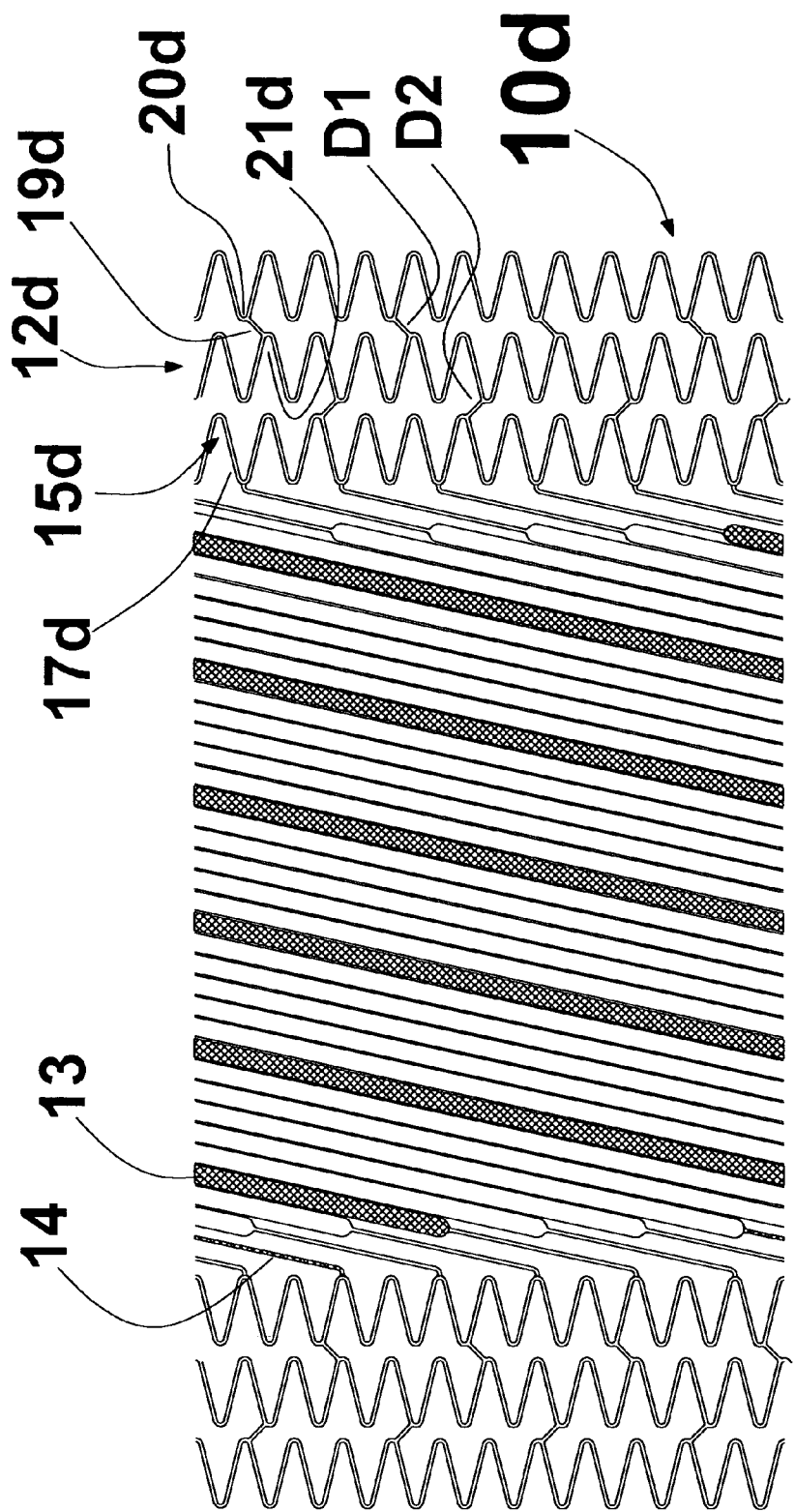
FIG. 1D is a plan view of an alternate embodiment of the strut members and flexible linking elements including multiple strut ring portions.

Any number of strut ring portions 15 and 16 can be used in strut member 12. For example, strut member 12c can comprise a single strut ring portion 15c, as shown in FIG. 1C, a pair of strut ring portions 15 and 16, as shown in FIG. 1A, or multiple strut ring portions 15d connected together with connecting elements 19d, as shown in FIG. 1D. Connecting elements 19d connect adjacent strut ring portions 15d together diagonally at peaks 20d and 21d in either diagonal direction $D_1$ and/or diagonal direction $D_2$.

Helical elements 13 can be connected with linking element 14 to each respective strut element 17, as shown in FIG. 1A. Linking element 14 can be flexible. Alternatively, helical elements 13 can connect to some of strut elements 17 as shown in FIG. 1B. FIG. 1B illustrates an embodiment in which every other strut member 17 is connected with linking element 14 to helical element 13. It will be appreciated that alternate combinations of connections of helical elements 13 to some of strut elements 17 can be used in accordance with the teachings of the present invention.

In an alternate embodiment, strut members 12e can be flared to provide improved anchoring of stent 10e, as shown in FIG. 1E. In an alternate embodiment helical elements 13g have a larger diameter than strut member 12, as shown in FIG. 1G. In an alternate embodiment, strut members 12f can have a bulged configuration in which strut member 12f has a larger diameter than helical elements 13 to provide improved anchoring, as shown in FIG. 1F.

Strut member 12 can have additional features to provide improved anchoring in the vessel. For example, strut member 12g can include at least one barb 24 on distal end 22 and/or proximal end 23 of stent 10g, as shown in FIGS. 1H and 1I.

Referring to FIG. 1A, linking elements 14 connect strut members 12 to helical elements 13. Linking elements 14 allow the helix angle of helical elements 13 to change as the diameter of stent 10 increases during expansion. Linking elements 14 can be straight or curved.

Pitch of helical elements 13 is related to the diameter of stent 10 and helix angle of helical elements 13 by the following formula:

$$\text{Pitch} = \pi D \tan(\theta) \qquad (1)$$

wherein θ is the helix angle, as shown in FIG. 1A, of the helical elements and D is the diameter of the stent.

The Diameter of stent 10 and Helix angle of helical elements 13 in an expanded and a crimped state are related by the following formula:

$$De/\cos(\theta e) = Dc/\cos(\theta c) \qquad (2)$$

wherein De is the expanded stent diameter, θe is the expanded helix angle, Dc is the crimped diameter and θc is the crimped helix angle.

As stent 10 is expanded the diameter of stent 10 gets larger and the helix angle of helical elements 13 decreases. The crimped diameter is limited by the helix angle, the width of helical elements 13 and number of helical elements 13.

During use, stent 10 comprised of helical elements 13 and linking elements 14 provides a high percentage of vessel covered by the stent, for example, such as a vessel near an aneurysm. For example, the percentage of the portion of the vessel covered by the helical elements of the stent can be in the range of about 35% to about 90%. Preferably, the percentage of the portion of the vessel covered by the helical elements of the stent is at least about 50%. Stent 10 provides an open area of about 10% to about 65%.

Linking element 14 can have a length and shape to minimize the strain and optimize the expansion behavior of stent 10. Linking element 14 can have a thickening which varies along the length of linking element 14. This can include relatively straight and long links having a length of about 25% to about 50% of the circumference of stent 10. Linking element 14 can also comprise relatively straight and short links having a length in the range of about 10% to about 25% of the circumference of stent 10. Alternatively, linking elements 14 can comprise curved links as described below.

FIG. 2A is a plan view of an alternate embodiment of stent 30. Stent 30 comprises helical element 33. Helical element 33 is split into two segments 34 and 35. FIG. 2B is a detailed view showing the two segments 34 and 35 comprising helical element 33. Splitting helical element 33 into a pair of segments improves crimping and expansion characteristics of stent 30, allowing helical element 33 to more easily change helix angle as the diameter of stent 30 expands from a crimped state to an expanded state. In an alternative embodiment, helical elements 33c can be split into a plurality of segments 34c, 35c, and 36c to provide additional improvement in the crimping and expansion characteristics, as shown in FIG. 2C.

Figure 3:
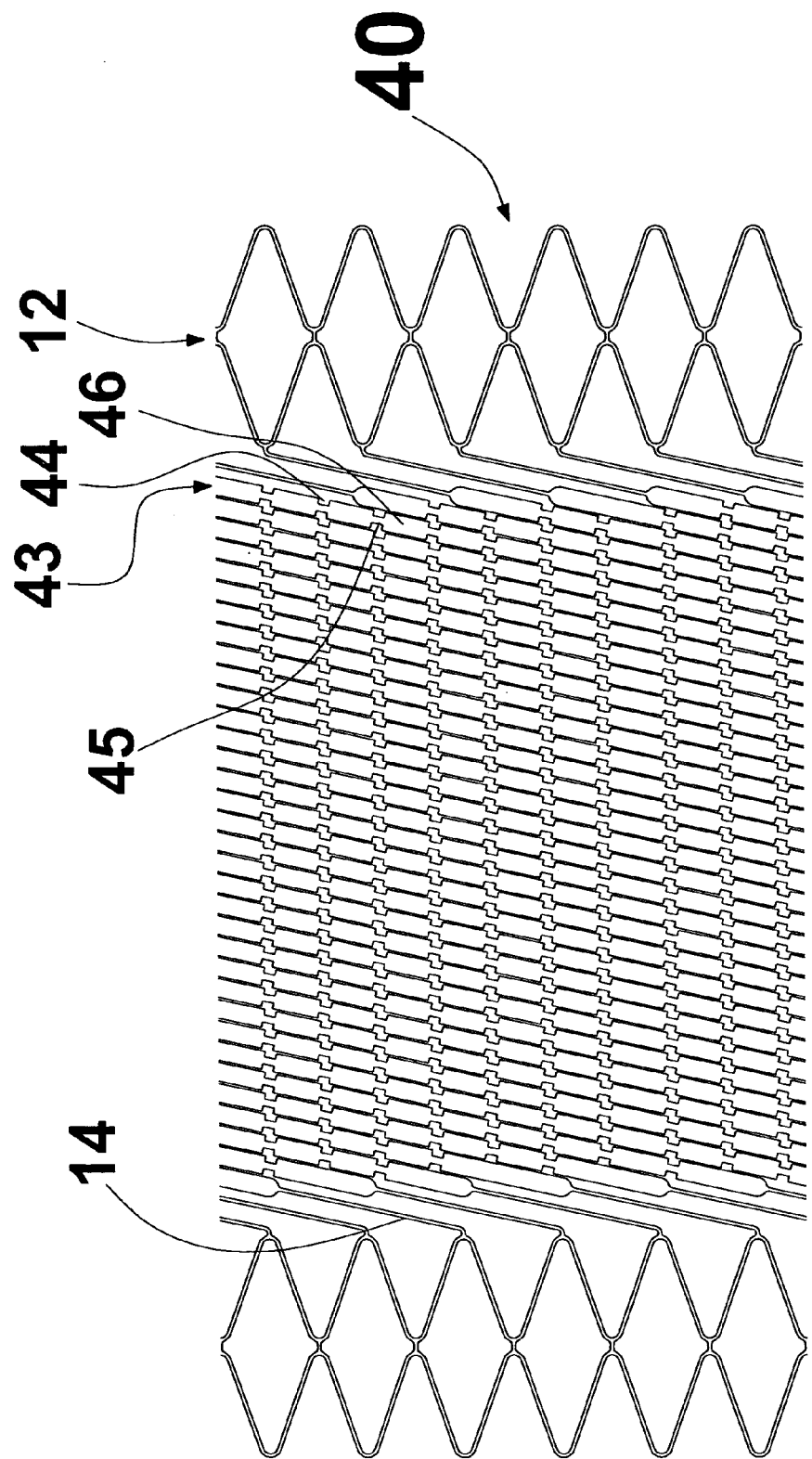
FIG. 3 is a plan view of an alternate embodiment of the present invention having helical elements with thin sections interposed between strut members and connected to the strut members by flexible linking elements.

FIG. 3 is a plan view of an alternate embodiment of stent 40. Stent 40 comprises helical elements 43 having notches 44 at points along its length. Notches 44 create thin sections 45 of helical element 43. For example, thin sections 45 can have a thickness of about 10% to about 80% of the adjacent thicker portion 46 of helical element 43. Thin sections 45 created by notches 44 can act as hinge points and offers improved crimping and expansion characteristics allowing the helix angle of helical element 43 to more easily change helix angle as the diameter of stent 40 expands from a crimped state to an expanded state. In one embodiment, notches 44 can be rectangular. Alternatively, thin sections 45 can be curved, circular, square, rectangular with fillets, and the like, and still provide improved crimping and expansion characteristics with different strain profiles.

FIG. 4 shows an embodiment in which thin sections 45 are diagonal, for connecting adjacent portions 46a and 46b of helical element 43. Sections 45 have a thickness of about 10% to about 80% of portions 46a and 46b. Curved linking elements 51 connect helical elements 43 to strut member 12.

Figure 5A:
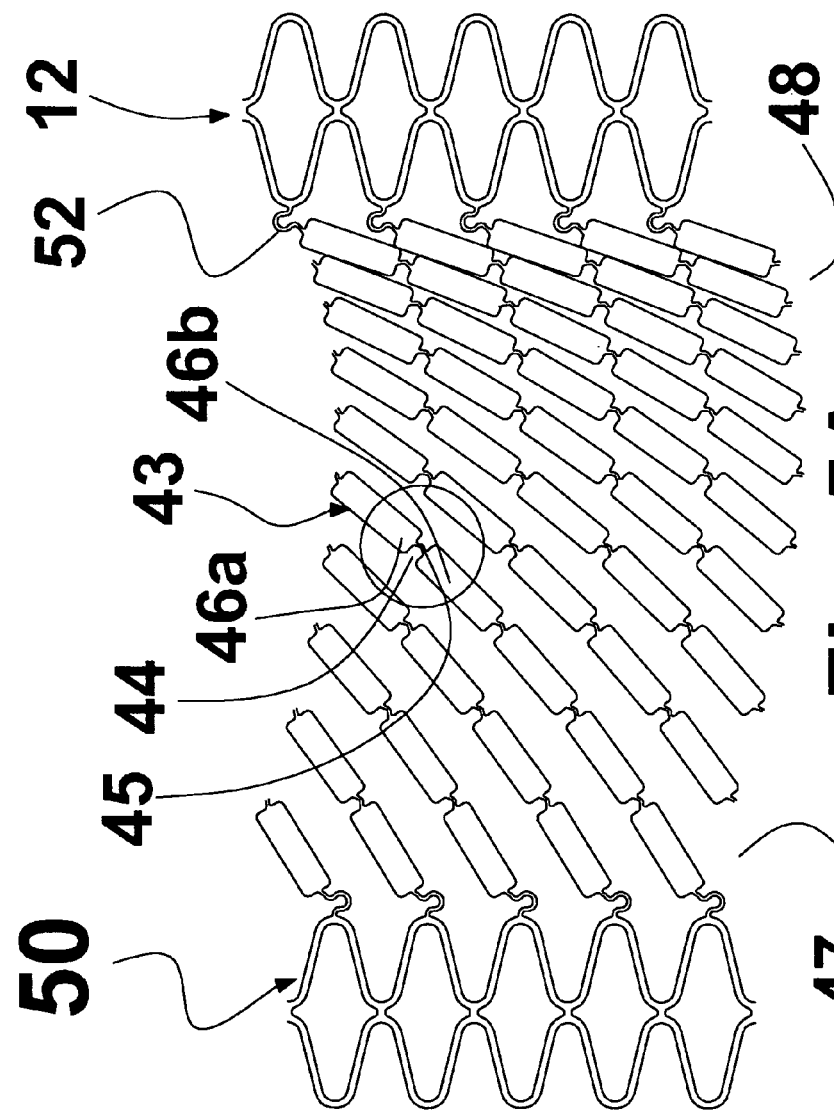
FIG. 5A is a plan view of an alternate embodiment of the present invention having a variable pitch of helical elements including curved sections having a reduced width and curved flexible linking elements connecting the helical elements to the strut members.
Figure 5B:
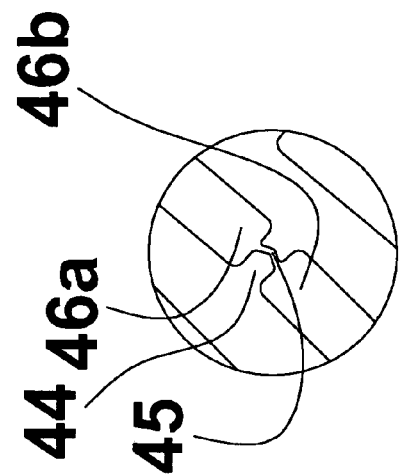
FIG. 5B is a detail view of FIG. 5A showing the helical elements including curved sections having a reduced width

FIG. 5A shows an embodiment in which thin sections 45 are curved and have a thickness of about 10% to about 80% adjacent portions 46. In this embodiment, the pitch of helical element 43 changes along the length of stent 50 where the pitch is longer on left hand side 47 of stent 50 and shorter on right hand side 48 of stent 50. Varying the pitch in this manner changes the percent of vessel coverage along the length of the stent. This may be advantageous in an embodiment for treating an aneurysm, in which right hand side 48 of stent 50 including a short pitch section could be placed at an up-stream side of the aneurysm for effectively cutting off blood flow to the aneurysm, and left hand side 47 of stent 50 can be used in the down stream side for not entirely covering the aneurysm or vessel wall with stent material. Stent 50 also has curved flexible linking elements 52 connecting helical element 43 to strut member 12. FIG. 5B is a detailed view of thin section 45 of stent 50.

The helical stents of the present invention may be placed within vessels using procedures well known in the art. The helical stents may be loaded into the proximal end of a catheter and advanced through the catheter and released at the desired site. Alternatively, the stent may be carried about the distal end of the catheter in a compressed state and released at the desired site. The stent may either be self-expanding or expanded by means such as an inflatable balloon segment of the catheter. After the stent(s) has been deposited at the desired intralumenal site, the catheter is withdrawn.

The self expanding embodiment of the stent would not necessarily require additional expansion methods. However, the balloon expanding embodiment can use additional expansion methods. Expansion methods for a balloon expanding embodiment of the present invention are described below.

Figure 6A:
FIG. 6A is a schematic diagram of a balloon expanding stent delivery system before inflation of the balloon with a stent on the balloon.
Figure 6B:
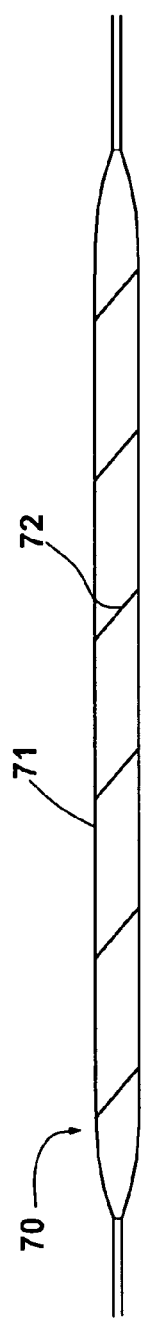
FIG. 6B is a schematic diagram of a balloon expanding stent delivery system before inflation of the balloon without a stent on the balloon.
Figure 6C:
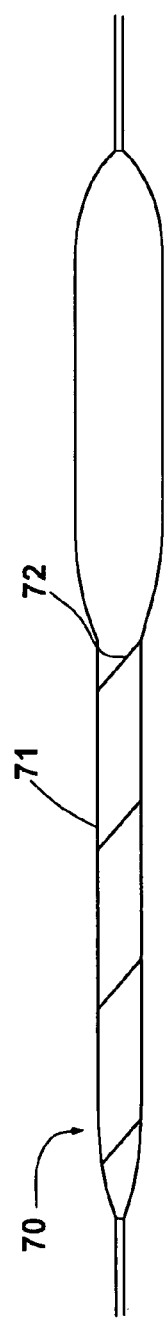
FIG. 6C is a schematic diagram of a balloon expanding stent delivery system after partial inflation of the balloon without a stent on the balloon.
Figure 6D:
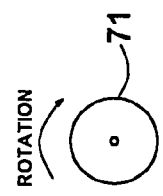
FIG. 6D is an end view of FIG. 6C showing the rotation of the balloon expanding stent delivery system.

In a balloon expanding embodiment of the present invention, a balloon expands the diameter of the stent and also rotates the helical elements such that the helix angle decreases, the pitch between helical elements shortens and the stent provides the desired vessel coverage of at least about 35% to about 90%, preferably about 50% of the portion of the vessel covered by the helical elements of the stent. FIG. 6A illustrates a balloon expanding delivery system 70 with a stent 40 mounted on the system. FIG. 6B illustrates balloon expanding delivery system 70 in a pre-inflated state, stent 40 has been omitted for clarity. Balloon 71 includes twists 72 which rotate in an opposite direction of helical elements 43. Twisted balloon 71 is placed within stent 40, as shown in FIG. 6A. Balloon 71 is inflated to an inflated state, as shown in FIG. 6C. As balloon 70 is inflated it rotates, as shown in FIG. 6D, imparting to stent 40 a torque so as to rotate helical elements 43 to a smaller helix angle, thereby shortening the helical pitch so as to provide the desired vessel coverage.

A conventional self expanding stent delivery system utilizes an outer sheath to hold the stent in a crimped (radially compact) state and a pusher positioned at the proximal end of the stent which react the forces developed as the outer sheath is retracted during stent deployment. A conventional delivery system often has an inner tube which goes over a guide wire, also used during a typical procedure.

Figure 7A:
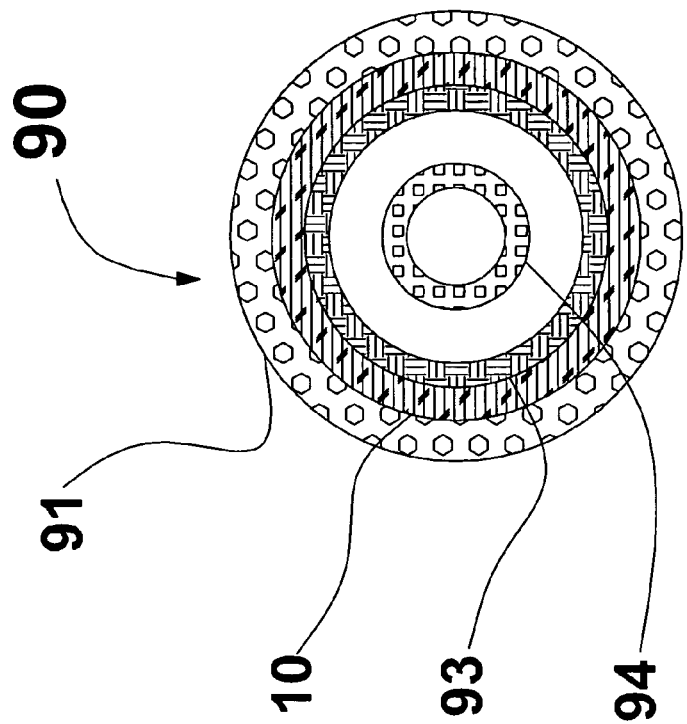
FIG. 7A is an end cross section schematic representation of a self-expanding stent delivery system of the present invention prior to stent deployment.
Figure 7B:
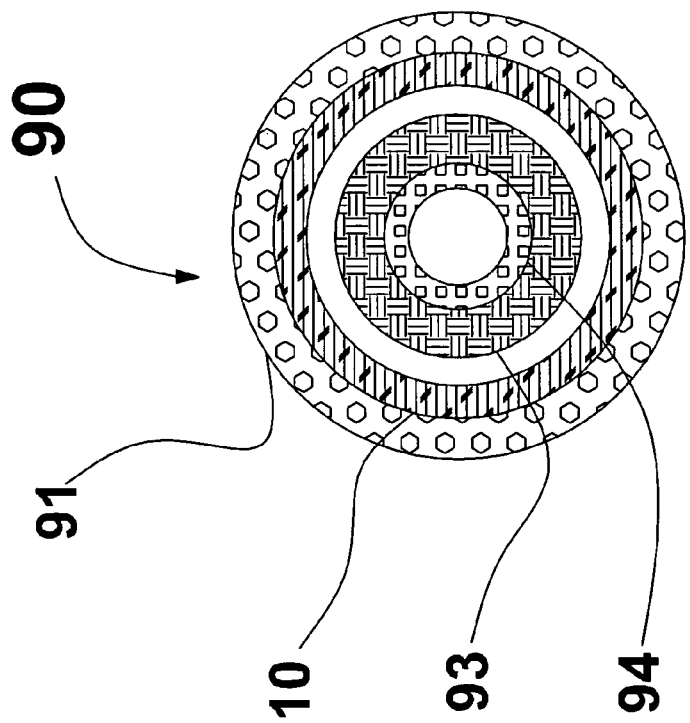
FIG. 7B is an end cross section schematic representation of a self-expanding stent delivery system of the present invention during stent deployment.

FIGS. 7A and 7B are cross sectional schematic representations illustrating self-expanding stent delivery system 90. FIG. 7A shows stent 10 crimped and positioned within outer sheath 91. Pusher balloon 93 is positioned within stent 10 in a deflated state. Pusher balloon 93 is adjacent inner tube 94. Inner tube 94 can be a tube for a guide wire. Pusher balloon 93 is sized such that it can replace or augment the pusher positioned at the proximal end of the stent in a conventional delivery system as described above.

In FIG. 7B pusher balloon 93 is inflated to a diameter about the same as the inside diameter of stent 10 in a crimped state. Pusher balloon 93 in its inflated state can distribute the reaction force developed during retraction of outer sheath 91 over the length of stent 10 instead of only at the proximal end. Accordingly, stent 10 does not significantly deform even though the axial stiffness of stent 10 is relatively low.

In an alternative embodiment, fluid used to inflate pusher balloon 93 can be chilled to a temperature in the range of about −10° C. to 10° C., thereby lowering the temperature of stent 10, reducing the outward force that stent 10 exerts on outer sheath 91, and lowering the reaction force developed to retract outer sheath 91.

The stent of the present invention may be placed within body lumen such as neurovascular vessels of non-neurovascular vessels of any mammal species including humans, without damaging the lumenal wall. For example, the stent can be placed within a lesion or an aneurysm for treating the aneurysm. In one embodiment, the stent can be placed within a brain aneurysm for treating the brain aneurysm. In one embodiment, the stent can be placed in a super femoral artery. Upon insertion into the vessel, the stent provides coverage of at least about 35% to about 90% of the portion of the vessel covered by the helical elements of the stent, preferably at least about 50% of the portion of the vessel covered by the helical elements of the stent.

The stent of the present invention can be formed of any biocompatible material, such as stainless steel, titanium, gold, nickel-titanium (often referred to as shape-memory metal or "nitinol") alloys, plastics and combinations thereof.

It is to be understood that the above-described embodiments are illustrative of only a few of the many possible specific embodiments, which can represent applications of the principles of the invention. Numerous and varied other arrangements can be readily devised in accordance with these principles by those skilled in the art without departing from the spirit and scope of the invention.

What is claimed is:

1. A radially expandable stent comprising:
   a plurality of strut members;
   a plurality of side by side helical elements extending helically about an axis of said strut members and interposed between said strut members, said strut members comprising a plurality of strut elements; and
   a helix angle, said helix angle being an acute angle formed between a plane perpendicular to an axis of said stent and said helical element;
   said helical elements comprise a plurality of side by side elongated elements along a length of said helical elements, each of said helical elements being connected to each of said strut elements with side by side elongated flexible curved linking elements providing a radially expandable tubular structure, said side by side elongated linking elements are thinner in width than said helical elements;
   wherein when said stent is radially expanded from a crimped state, a diameter of said stent increases and the helix angle of each of the helical elements in an expanded state decreases from the helix angle in a crimped state.

2. The stent of claim 1 wherein said strut members comprise one or more strut ring portions, said strut ring portions being radially expandable.

3. The stent of claim 2 wherein said linking elements connect said strut ring portions to one another at peaks of said strut ring portions.

4. The stent of claim 2 wherein said one or more strut ring portions wrap around a circumference of said stent.

5. The stent of claim 2 wherein said one or more strut ring portions wrap in a spiral around a circumference of said stent.

6. The stent of claim 2 wherein said strut ring portions comprise multiple strut ring portions and connecting elements diagonally connect said strut ring portions to one another at peaks of said strut ring portions in a first diagonal direction and a second diagonal direction.

7. The stent of claim 1 wherein said strut members are flared.

8. The stent of claim 1 wherein said strut members have a larger diameter than said helical elements.

9. The stent of claim 1 wherein said helical elements have a larger diameter than said strut members.

10. The stent of claim 1 wherein at least one of said strut members include at least one barb.

11. The stent of claim 1 wherein a pitch of said helical elements changes along a length of said stent.

12. The stent of claim 11 wherein a pitch of said helical elements is longer on one side of said stent and said pitch of said helical elements is shorter on the other side of said stent.

13. The stent of claim 1 wherein said helical elements have a constant pitch.

14. The stent of claim 1 wherein said helical elements have a variable pitch.

15. The stent of claim 1 wherein said helical elements comprise straight sections, curved sections or both straight sections and curved sections.

16. A method for placing a stent within a mammal in a body lumen comprising placing one or more stents in said body lumen, said stent comprising:
   a plurality of strut members; and
   a plurality of side by side helical elements extending helically about an axis of said strut members and interposed between said strut members, said strut members comprising a plurality of strut elements;
   a helix angle, said helix angle being an acute angle formed between a plane perpendicular to an axis of said stent and said helical element;
   said helical elements comprise a plurality of side by side elongated elements along a length of said helical element, each of said helical elements being connected to each of said strut elements with side by side elongated flexible curved linking elements providing a radially expandable tubular structure, said side by side elongated linking elements are thinner in width than said helical elements;
   wherein when said stent is radially expanded from a crimped state, a diameter of said stent increases and the helix angle of each of the helical elements in an expanded state decreases from the helix angle in a crimped state.

17. The method of claim 16 wherein said inserted stent covers at least about 35% to about 90% of a portion of said body lumen and wherein the mammal is a human and the body lumen is a vessel or duct.

18. The method of claim 16 wherein said inserted stent covers at least about 35% to about 90% of a portion of said body lumen and wherein the mammal is a human and the body lumen is a brain aneurysm.

19. The method of claim 16 wherein said inserted stent covers at least about 35% to about 90% of a portion of said body lumen and wherein the mammal is a human and the body lumen is an aneurysm.

20. The method of claim 16 wherein said inserted stent covers at least about 50% of a portion of said body lumen.

21. A method for treating a diseased vessel or duct in a mammal comprising the steps of:
   placing one or more stents at a target site, said stent comprising:
   a plurality of strut members; and
   a plurality of side by side helical elements extending helically about an axis of said strut members and interposed between said strut members, said strut members comprising a plurality of strut elements;
   a helix angle, said helix angle being an acute angle formed between a plane perpendicular to an axis of said stent and said helical element;
   said helical elements comprise a plurality of side by side elongated elements along a length of said helical element, each of said helical elements being connected to each of said strut elements with side by side elongated flexible curved linking elements providing a radially expandable tubular structure, said side by side elongated linking elements are thinner in width than said helical elements;
   wherein when said stent is radially expanded from a crimped state, a diameter of said stent increases and the helix angle of each of the helical elements in an expanded state decreases from the helix angle in a crimped state.

22. The method of claim 21 wherein said stent covers about 35% to about 90% of a portion of said target site.

23. The method of claim 21 wherein said stent covers at least about 50% of a portion of said target site.

24. The method of claim 21 wherein said inserted stent covers at least about 35% to about 90% of a portion of said body lumen and wherein the mammal is a human and the body lumen is a brain aneurysm.

25. The method of claim 21 wherein said inserted stent covers at least about 35% to about 90% of a portion of said body lumen and wherein said target site is an aneurysm.

26. The method of claim 21 wherein said inserted stent covers at least about 35% to about 90% of a portion of said body lumen and wherein said target site is a vascular site.

27. The method of claim 21 wherein said inserted stent covers at least about 35% to about 90% of a portion of said body lumen and wherein the target site is a super femoral artery.

28. The method of claim 21 wherein said inserted stent covers at least about 35% to about 90% of a portion of said body lumen and wherein the target site is a lesion.

29. The method of claim 21 wherein said inserted stent covers at least about 35% to about 90% of a portion of said body lumen and wherein the target site is a non-vascular site.

* * * * *